United States Patent
Kuth

(10) Patent No.: US 6,999,610 B2
(45) Date of Patent: Feb. 14, 2006

(54) DEVICE FOR AUTOMATICALLY SORTING PERIODIC DATA RECORDS

(75) Inventor: Rainer Kuth, Herzogenaurach (DE)

(73) Assignee: Siemens Aktiengesellschaft, Munich (DE)

(*) Notice: Subject to any disclaimer, the term of this patent is extended or adjusted under 35 U.S.C. 154(b) by 637 days.

(21) Appl. No.: 09/982,912

(22) Filed: Oct. 22, 2001

(65) Prior Publication Data

US 2002/0047698 A1    Apr. 25, 2002

(30) Foreign Application Priority Data

Oct. 20, 2000 (DE) ............................... 100 52 870

(51) Int. Cl.
*G06K 9/00* (2006.01)

(52) U.S. Cl. .................... 382/132; 382/107; 382/199; 382/207; 128/922

(58) Field of Classification Search ............... 382/107, 382/128, 131, 132, 159, 165, 170, 181, 190, 382/191, 199, 203, 207, 286; 128/920, 922
See application file for complete search history.

(56) References Cited

U.S. PATENT DOCUMENTS

| 3,575,162 A * | 4/1971 | Gaarder ..................... 600/479 |
| 4,855,910 A * | 8/1989 | Bohning ..................... 324/309 |
| 5,162,723 A | 11/1992 | Marzalek et al. ........ 324/76.19 |
| 6,252,924 B1 * | 6/2001 | Davantes et al. ............... 378/8 |
| 6,289,135 B1 * | 9/2001 | Declerck et al. ............ 382/276 |
| 6,674,879 B1 * | 1/2004 | Weisman et al. ........... 382/128 |

FOREIGN PATENT DOCUMENTS

EP          0 343 683          11/1989

* cited by examiner

*Primary Examiner*—Brian Werner
*Assistant Examiner*—Christopher Lavin
(74) *Attorney, Agent, or Firm*—Young & Thompson

(57) ABSTRACT

Device for automatically sorting periodic data records, in particular for representing the motion of parts in the human body from individual images, an examination monitor with a storage device for the data records been assigned a measuring and evaluation device which measures in the data records two separate points or a line of the moving part and, on the basis of their changes in distance or phase shifts, sorts the data records into a cyclic sequence.

10 Claims, 1 Drawing Sheet

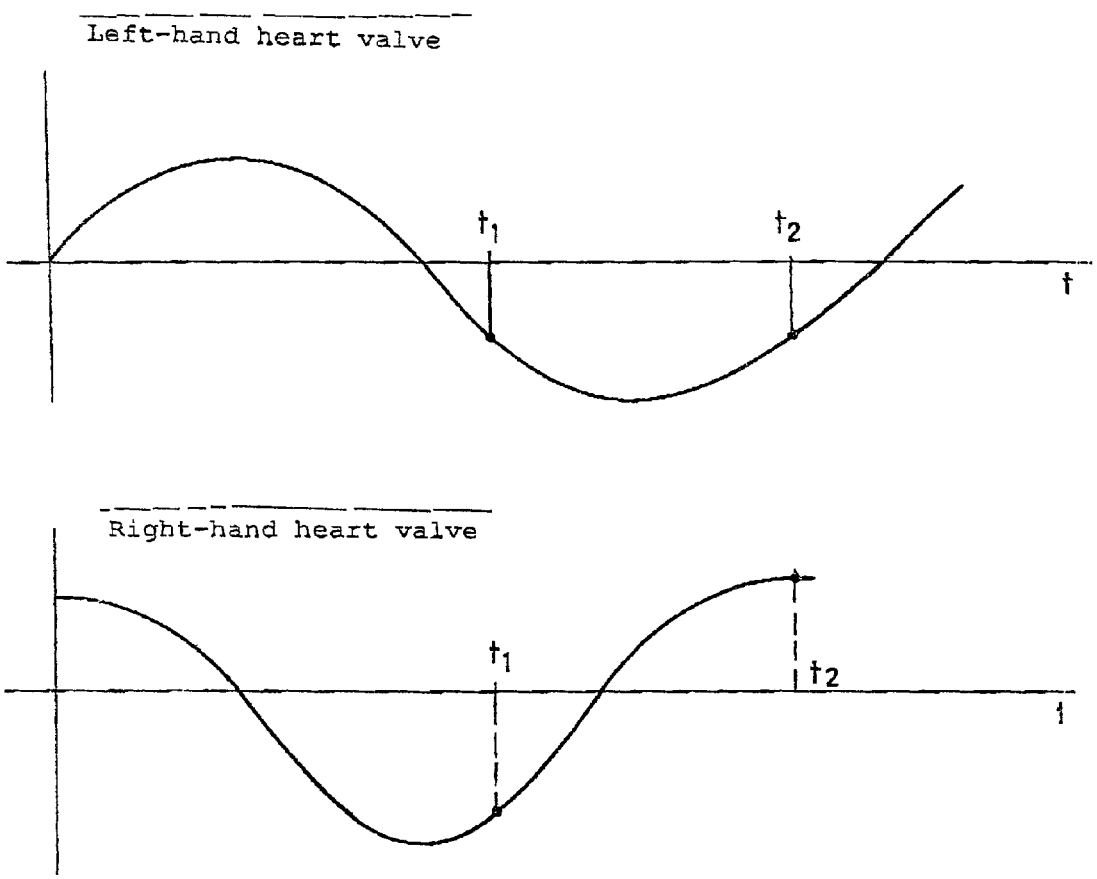

DEVICE FOR AUTOMATICALLY SORTING PERIODIC DATA RECORDS

The invention relates to a device for automatically sorting periodic data records, in particular for representing the motion of parts in the human body from individual images.

It is desired in the case of periodic movements of an object to acquire these in an imaging system in the form of many individual instantaneous pictures (images) and to analyze and examine these afterwards in a computer. If the image phases are correctly recorded, they can be evaluated subsequently in the appropriate way. However, in may cases they cannot be recorded in correct phase relationship, for example when a periodic process is being recorded stroboscopically without a defined frequency and phase relationship, or when individual images of X-ray pictures, in particular of MR pictures, are involved which have been produced without an EGC monitor for the reference points.

To date, series of images or, very generally, of data records, of a periodic process have been arranged only by hand but, in the case of the said example from MR tomography, this causes such an enormous complication that it cannot be implemented in practice.

It is therefore the object of the invention to create a device for automatically sorting periodic data records in the case of which it is possible to perform sorting even without records in correct data relationship.

In order to achieve this object, it is provided according to the invention that an examination monitor with a storage device for the data records is assigned a measuring and evaluation device which measures in the data records two separate points or a line, or the like, of a moving part and, on the basis of their changes in distance or phase shifts, sorts the data records into a cyclic sequence, it being possible for these cyclically ordered data records then to be combined simply one after another to form a film.

Particularly in the field of technology, it would be possible, for example, for the purpose of measuring the stress on workpieces such as an engine with pistons to make the latter from a special plastic and photograph them in polarized light, but it can also be expedient in the case of the representation of the motion of parts in the human body to use an input device to prescribe the waveform on which the periodicity is based, with triangles, rectangles or sinusoidal curves chiefly coming into consideration as waveforms. Specifically in the case of waveforms having at least horizontal rectangular components, it is possible in the process to determine the frequency distribution of the parameters and to establish therefrom the relative width of the horizontal plateaux.

The invention is to be explained in more detail below with the aid of the drawing, which shows a diagram with the movement of a point of the left-hand heart valve at the top, and below that to the movement of a point of the right-hand heart valve.

Assuming that an MR data record has been made at the instant t1 and at the instant t2 (these times themselves not being known), the images of the said point of the left-hand heart valve would be situated wholly at the same point, that is to say the image data records do not differ here at all from one another, and it is not known whether the movement takes place toward the maximum or away from the maximum further toward the X-axis. This would prevent sorting of the data records solely on the basis of the measurement of the left-hand heart valve. However, if a point of the right-hand heart valve is also considered at the same time, at the instant t1 and t2 the images of this point are very different, that is to say the measurement of two separate points of a moving part, such as the human heart in the present case, renders it possible to sort the data records into a cyclic sequence by the changes in distance or phase shifts.

What is claimed is:

1. A device for automatically sorting individual images of a moving part that moves in a periodic manner, comprising:
   an examination monitor having a storage device for data records representing the individual images; and
   a measuring and evaluation device which identifies in the data records at least one feature of the moving part appearing in the individual images, and sorts the data records from multiple cycles into a single cyclic sequence based only on displacement of the at least one feature between different said images represented by the data records and a periodicity of the moving part.

2. The device as claimed in claim 1, wherein the cyclically ordered data records are combined to form a film.

3. The device as claimed in claim 1, wherein a waveform on which the periodicity is based can be prescribed by an input device.

4. The device as claimed in claim 3, wherein the waveforms comprise triangles, rectangles or sinusoidal curves.

5. The device as claimed in claim 1, wherein the data records represent images recorded stroboscopically without defined frequency and phase relationships with the motion of the moving part.

6. The device as claimed in claim 1, wherein the data records are individual images of X-ray pictures.

7. The device as claimed in claim 1, wherein the data records represent individual MR images.

8. The device of claim 1, wherein the data records represent images captured without defined frequency and phase relationships with the motion of the moving part.

9. The device of claim 1, wherein the feature includes at least one of a line and two separate points of the moving part and the displacement of the at least one feature is defined by at least one of distance and phase shifts.

10. The device of claim 5, wherein the at least one feature includes at least one of a line and two separate points of the moving part appearing in the individual images, and the displacement of the at least one feature is defined by at least one of distance and phase shifts.

* * * * *